(12) United States Patent
Kurt et al.

(10) Patent No.: US 9,186,127 B2
(45) Date of Patent: Nov. 17, 2015

(54) ULTRASONIC DIAGNOSIS APPARATUS AND METHOD OF CONTROLLING OUTPUT OF ULTRASONIC DIAGNOSIS APPARATUS

(75) Inventors: Sandstrom Kurt, Seoul (KR); Dae Young Kim, Chuncheon-si (KR); Soo Hwan Shin, Seoul (KR); Tae-Yun Kim, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 438 days.

(21) Appl. No.: 13/108,427

(22) Filed: May 16, 2011

(65) Prior Publication Data
US 2012/0197122 A1 Aug. 2, 2012

(30) Foreign Application Priority Data
Jan. 31, 2011 (KR) .......................... 10-2011-0009323

(51) Int. Cl.
*A61B 8/00* (2006.01)
*A61B 5/00* (2006.01)
(Continued)

(52) U.S. Cl.
CPC . *A61B 8/54* (2013.01); *A61B 8/465* (2013.01); *A61B 8/467* (2013.01); *A61B 8/56* (2013.01); *A61B 8/585* (2013.01); *G01S 7/5205* (2013.01); *A61B 8/4444* (2013.01)

(58) Field of Classification Search
CPC ...... A61B 8/546; A61B 8/4444; A61B 8/467; A61B 8/465; A61B 8/56; G01S 7/5205; G01S 7/52096; G01S 15/8979
USPC .............................. 600/443, 438, 437; 604/22
See application file for complete search history.

(56) References Cited

U.S. PATENT DOCUMENTS 6,669,638 B1 * 12/2003 Miller et al. .................. 600/438
6,824,518 B2 * 11/2004 Von Behren et al. ......... 600/443
(Continued)

FOREIGN PATENT DOCUMENTS

CN 101601594 A 12/2009
EP 1693004 A1 8/2006
(Continued)

OTHER PUBLICATIONS

International Search Report and Written Opinion thereof issued in International Patent Application No. PCT/KR2011/009151 dated Jun. 20, 2012.

(Continued)

*Primary Examiner* — Long V Le
*Assistant Examiner* — Helene Bor
(74) *Attorney, Agent, or Firm* — McDermott Will & Emery LLP

(57) ABSTRACT

Provided is a method of controlling voltage levels of overall outputs in a combinational mode, in an ultrasonic diagnosis apparatus that may operate in the combinational mode. A judging unit of the ultrasonic diagnosis apparatus may judge whether at least a part of individual modes included in the combinational mode exceeds a threshold determined by safety standards, in accordance with an inputted overall output voltage level control command. When it is judged that at least the part of the individual modes exceeds the threshold determined by the safety standards, an output control unit may maintain an individual output with respect to the at least the part, among the voltage levels that may be outputted from a transducer, to be below the threshold, so that the individual output may be below the standards in accordance with the overall output control command.

10 Claims, 6 Drawing Sheets

(51) Int. Cl.
*A61B 17/00* (2006.01)
*G01S 7/52* (2006.01)

(56) References Cited

U.S. PATENT DOCUMENTS

| | | | |
|---|---|---|---|
| 8,128,565 B2* | 3/2012 | Ohtake et al. | 600/441 |
| 2004/0102703 A1 | 5/2004 | Behren et al. | |
| 2007/0016021 A1 | 1/2007 | Moritz | |
| 2007/0112266 A1* | 5/2007 | Kishimoto | 600/437 |
| 2007/0160540 A1 | 7/2007 | Nishigaki et al. | |
| 2009/0082670 A1* | 3/2009 | Kamiyama et al. | 600/445 |
| 2009/0171214 A1 | 7/2009 | Kim et al. | |

FOREIGN PATENT DOCUMENTS

| | | |
|---|---|---|
| JP | 2004-201714 A | 7/2004 |
| JP | 2005-058332 A | 3/2005 |
| JP | 2005-334197 A | 12/2005 |
| JP | 2009-160401 A | 7/2009 |
| JP | 2009-261800 A | 11/2009 |

OTHER PUBLICATIONS

First Office Action dated Nov. 3, 2014 issued in Japanese Patent Application No. 201180066513.7 (English translation).

* cited by examiner

ULTRASONIC DIAGNOSIS APPARATUS AND METHOD OF CONTROLLING OUTPUT OF ULTRASONIC DIAGNOSIS APPARATUS

CROSS-REFERENCE TO RELATED APPLICATION

This application claims the benefit of Korean Patent Application No. 10-2011-0009323, filed on Jan. 31, 2011, in the Korean Intellectual Property Office, the disclosure of which is incorporated herein by reference.

BACKGROUND

1. Field of the Invention

The present invention relates to an ultrasonic diagnosis apparatus, and more particularly, to a method of effectively controlling an acoustic output of the ultrasonic diagnosis apparatus by setting an individual output in a combinational mode that may provide at least two pulser output signals in accordance with safety standards, such as a mechanical index (MI), a thermal index (TI), and the like, which may be determined by international regulatory standards, for example National Electrical Manufacturers Association (NEMA), International Electrotechnical Commission (IEC), Food and Drug Administration (FDA), and the like.

2. Description of the Related Art

An ultrasonic diagnosis apparatus is an apparatus for transmitting, from the surface of a body of an object, an ultrasonic wave signal toward a predetermined structure inside the body, and for obtaining an image with respect to a cross section of soft tissues or a blood flow using information of the ultrasonic wave signal reflected from the tissues of the body.

This ultrasonic diagnosis apparatus has advantages of a small size, a low cost, a real-time display, and a high stability without exposing patients and users to X-ray radiation and the like, and thus, the ultrasonic diagnosis apparatus is widely used along with other diagnostic imaging systems such as an X-ray diagnosis equipment, a computerized tomography (CT) scanner, a magnetic resonance imaging (MRI) equipment, a nuclear medicine diagnosis equipment, and the like.

Generally, an acoustic output of an ultrasonic diagnosis apparatus is limited and determined by international standards, for example, a mechanical index (MI). Here, the MI corresponds to an index that may quantize effects of mechanical factors, which an ultrasonic wave may have, on a human body. As another example of the international standards, there also exists a thermal index (TI). As is commonly known, the international permissible standards for the MI and the TI may correspond to an MI of less than 1.9 and a TI of less than 6.0.

The ultrasonic diagnosis apparatus may diagnose an object more precisely by increasing a transmission voltage of a pulser and consequently an acoustic output. When the transmission voltage is increased, quality of an image may become higher. However, a problem may occur in that values of items of the safety standards such as the MI, the TI, and the like may proportionally increase.

The high values of the items may indicate that the ultrasonic diagnosis apparatus may have a greater effect on the human body, and accordingly the use of the corresponding ultrasonic diagnosis apparatus may be limited by the international standards when the values are greater than a predetermined level.

The ultrasonic diagnosis apparatus may operate in several modes, such as a brightness (B) mode, a power Doppler (pD) mode, and the like, and may also operate in combinational modes, such as a B+pD mode or a B+pD+CD mode according to a choice of a user. The CD mode may refer to a color Doppler mode.

In the combinational modes, pulses having at least two levels of voltage outputs may be outputted, and the outputted voltage may be needed to be controlled so that an individual voltage output may be within international regulatory standards.

SUMMARY

An aspect of the present invention provides a method of controlling an output of an ultrasonic diagnosis apparatus, and the ultrasonic diagnosis apparatus by the method, with respect to the output of the ultrasonic diagnosis apparatus that may operate in a combinational mode, so that an overall power may be controlled, and an individual output level may satisfy international regulatory standards.

Another aspect of the present invention also provides an ultrasonic diagnosis apparatus that may enhance convenience of a user by efficiently providing a user interface (UI) in order to control an output in a combinational mode.

According to an aspect of the present invention, there is provided an ultrasonic diagnosis apparatus that may operate in a combinational mode and may simultaneously provide voltage levels of a plurality of outputs using a transducer, including a UI to receive an output value control command with respect to all of the plurality of the outputs, a judging unit to judge whether the output value control command corresponds to a command that may enable the voltage levels of the outputs corresponding to a first mode, included in the combinational mode, to exceed a threshold determined by safety standards with respect to the first mode, and an output control unit to maintain the outputs corresponding to the first mode to be below the threshold, and to perform an output control based on the output value control command with respect to other outputs included in the combinational mode excluding the first mode, when the output value control command corresponds to a value that may enable the voltage levels of the outputs corresponding to the first mode to exceed the threshold determined by the safety standards with respect to the first mode.

The combinational mode may correspond to any one of a brightness (B)+power Doppler (pD) mode, a B+color Doppler (CD) mode, and a B+pD+CD mode.

In this instance, the output value control command either may increase voltages of the overall outputs of the transducer corresponding to the combinational mode, or may lower the voltages of the overall outputs of the transducer corresponding to the combinational mode, by a percentage unit.

Also, the UI may include an output control interface corresponding to each of a plurality of modes included in the combinational mode, and an output control interface to adjust overall outputs of the plurality of the modes.

The first mode may correspond to a B mode, and the safety standards with respect to the first mode may correspond to a mechanical index (MI).

According to an aspect of the present invention, there is provided a method of controlling an output of an ultrasonic diagnosis apparatus that may operate in a combinational mode, and may simultaneously provide voltage levels of a plurality of outputs using a transducer, including receiving, by a UI of the ultrasonic diagnosis apparatus, an output value control command with respect to all of the plurality of the outputs, judging, by a judging unit of the ultrasonic diagnosis apparatus, whether the output value control command corresponds to a command that may enable the voltage levels of the outputs corresponding to a first mode, included in the combinational mode, to exceed a threshold determined by safety standards with respect to the first mode, and maintaining, by an output control unit of the ultrasonic diagnosis apparatus, the outputs corresponding to the first mode to be below the threshold, and performing an output control based on the output value control command with respect to other outputs included in the combinational mode excluding the first mode, when the output value control command corresponds to a value that may enable the voltage levels of the outputs corresponding to the first mode to exceed the threshold determined by the safety standards with respect to the first mode.

When the user controls the output of the ultrasonic diagnosis apparatus that may be operating in the combinational mode, in a case of increasing overall outputs, an automatic output control may be performed to maintain an individual output to be below a threshold determined by international regulatory standards, such as the MI, and the like so that safety of the diagnosis apparatus may be secured while the user controls the diagnosis apparatus to improve image quality.

Also, an efficient UI for an output control may be provided so that convenience of the user may be secured when the user controls the output for a medical reason.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Figure 1:
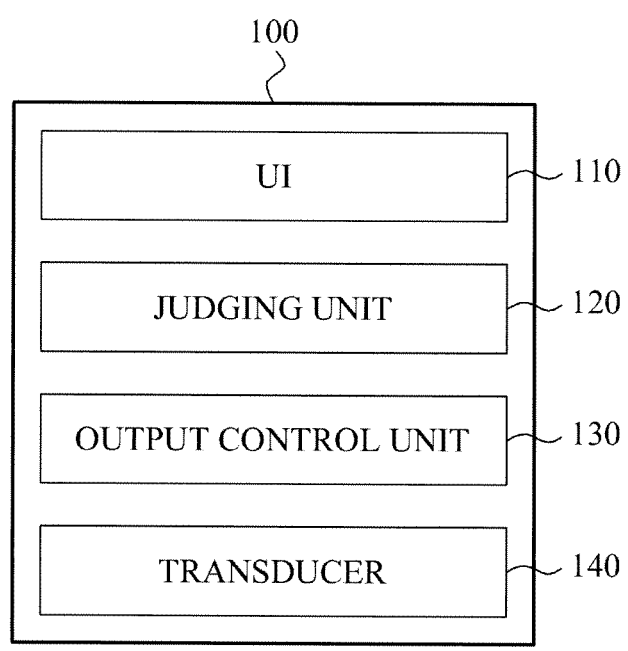
FIG. 1 is a diagram illustrating an ultrasonic diagnosis apparatus according to an embodiment of the present invention.

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

FIG. 1 is a diagram illustrating an ultrasonic diagnosis apparatus 100 according to an embodiment of the present invention.

The ultrasonic diagnosis apparatus 100 may selectively provide combinational modes as well as a single mode. For example, the combinational modes may include a brightness (B)+power Doppler (pD) mode, a B+color Doppler (CD) mode, and a B+pD+CD mode, and the like. In these combinational modes, voltage levels of outputs having at least two patterns may be simultaneously provided.

According to the U.S. FDA 510K guidance, and the like with respect to international regulatory standards for safety of an ultrasonic diagnosis apparatus, an output of the ultrasonic diagnosis apparatus may be prohibited from exceeding a maximum permissible value of the output according to predetermined safety standards.

For example, a mechanical index (MI) in a B mode may be needed to be maintained below 1.9.

However, a user of the ultrasonic diagnosis apparatus 100 may desire to increase image quality of a diagnosis image that may be provided by the ultrasonic diagnosis apparatus 100, or to increase an acoustic output of a transducer by increasing a voltage output of a pulser for other medical purposes.

When the ultrasonic diagnosis apparatus 100 is operating in an individual mode such as the B mode, the user may easily adjust the output level within the standards since the adjustment of the output level may be compared with standards for an individual output, such as the MI.

Conversely, when the user desires to increase overall output levels in a combinational mode, a problem may occur in that outputs in the individual mode, that is, the outputs corresponding to the B mode may exceed the standards with respect to the MI.

According to an embodiment of the present invention, in a case that the ultrasonic diagnosis apparatus 100 operates in the combinational mode, even when the user may increase an output through an overall output control, each output of individual pulsers may be to controlled to be below a threshold of the acoustic output with respect to each individual mode.

Meanwhile, the output of the ultrasonic diagnosis apparatus 100 may be an acoustic output, however, the output control according to an embodiment of the present invention may also be construed as a control of an output voltage for controlling the acoustic output in the ultrasonic diagnosis apparatus 100. Accordingly, unless otherwise mentioned, hereinafter the present invention should be construed as not being limited to controlling only the acoustic output of the ultrasonic diagnosis apparatus 100.

Embodiments of the present invention will be hereinafter described on the assumption that the ultrasonic diagnosis apparatus 100 may operate in the B+pD mode. However, the present invention should not be construed as being limited to this B+pD mode. Instead, it would be appreciated by those skilled in the art that changes may be made to these exemplary embodiments without departing from the principles and spirit of the invention, the scope of which is defined by the claims and their equivalents.

Furthermore, although the MI has been described as an example of the international regulatory standards with respect to an ultrasonic diagnosis apparatus, an equivalent principle may be applicable to any other international regulatory standards, such as a TI, and the like. Accordingly, changes may be made to these exemplary embodiments without departing from the principles and spirit of the invention, the scope of which is defined by the claims and their equivalents.

It may be assumed that the ultrasonic diagnosis apparatus 100 may operate in the B+pD mode, and a current overall output may correspond to 50%. The overall output of 50% may be a default value from factory that may be set with respect to the ultrasonic diagnosis apparatus 100.

In the case of the overall output of 50%, a B/M power may be set to 20%, and a C/D power may be set to 30%.

Here, an output control command to increase the overall output by 1.5 dB to approximately 70% may be received from the user.

Then, a judging unit 120 may judge whether each of the B/M power and the C/D power exceeds a maximum permissible value, that is, a threshold determined by safety standards, according to the received output control command, before an output control unit 130 may control an output of a transducer 140.

When the overall output is increased by 1.5 dB, the BIM power may be increased from 20% to 28%, and the C/D power may be increased from 30% to 42%. Here, neither the B/M power nor the C/D power may exceed the threshold determined by the safety standards.

The threshold may have a different value with respect to each mode. For example, the threshold with respect to the B/M power may be determined to be 32%. The threshold may be set in association with the maximum permissible value of 1.9 dB of the MI with respect to the B mode.

In a state where the B/M power may have increased to 28%, and the C/D power may have increased to 42%, the overall output increase command by 1.0 dB may be received again from the user using a user interface (UI) 110. The increase in the overall output by 1.0 dB may correspond to an increase in the overall output to approximately 89%.

Then, the judging unit 120 may judge again whether each of the B/M power and the C/D power exceeds the set threshold, according to the overall output increase command.

However, since the current B/M power may correspond to 28% and the maximum permissible value, that is, the threshold may be determined to 32%, the B/M power may exceed the threshold when there is an increase in the overall output by 1.0 dB.

Since the B/M power may be 32% by the output increase by 0.6 dB, and may be equivalent to the threshold, the judging unit 120 may judge that the currently inputted increase in the overall output by 1.0 dB may be impermissible.

Then, the output control unit 130 may increase the B/M power by 0.6 dB to fix the B/M power to 32%, and may increase the C/D power by 1.32 dB, which may be greater than 1.0 dB, to increase the C/D power to 57%.

The overall output may be increased to 89% whereas the B/M power may be fixed to 32%, which may be below the threshold, and the C/D power may be increased to 57%.

In this instance, the overall output increase command to increase the overall output to 100% may be received again from the user, using the UI 110.

When the overall output is increased to 100%, the judging unit 120 may judge that the output may be impossible to be further increased with respect to the B/M power that may already have reached the threshold of 32%.

The, the output control unit 130 may maintain the fixed B/M power of 32%, and may increase the C/D power to 68%, that is, by about 0.77 dB.

Then, the overall output may correspond to 100%, and also neither the B/M power nor the C/D power may exceed the threshold determined by the safety standards.

According to an embodiment of the present invention, there is also provided interfaces that may control outputs with respect to each individual mode, that is, each of the B/M power and the C/D power, as well as an overall output control interface, using the UI 110.

When the user judges that an output of the B/M power of approximately 20% may be sufficient, and desires to increase the C/D power to improve image quality, the user may input a command to lower the B/M power to 20% using an individual output control interface with respect to the B/M power.

When the output control command to lower the B/M power to 20% is received using the UI 110, the judging unit 120 may judge whether the maximum permissible threshold with respect to the safety standards may be exceeded even when the individual output, that is, the C/D power is increased to 80%.

When the judging unit 120 judges that the output may be below the maximum permissible threshold with respect to the safety standards, the output control unit 130 may lower the BIM power to 20% and increase the C/D power to 80%, by automatically controlling the transducer 140. In this instance, the C/D power may be additionally increased by approximately 0.71 dB.

As aforementioned in the foregoing embodiment, the permissible standards for each of the powers corresponding to the individual modes may be maintained to be below the threshold by adjusting the voltage levels of the outputs of the transducer 140.

However, according to another embodiment of the present invention, it may be possible to adjust an output frame of an individual mode.

For example, in the case that the B/M power of 32% and the C/D power of 68% are maintained, when the user desires to increase the C/D power, the output control unit 130 may lower an output frame of the B/M mode, or a duty cycle, thereby performing an adjustment similar to the aforementioned embodiment.

In the UI 110, there may be simultaneously provided an interface that may control overall outputs, and interfaces that may control individual outputs, during a combinational mode operation. However, when the ultrasonic diagnosis apparatus 100 operates in a single mode, only the interface that may control the overall outputs may be provided, and the interfaces that may control the individual outputs may not be provided since the overall output control may correspond to an individual output control, in an operation of the single mode, that is, the B mode operation.

The examples with respect to providing the output control of the UI 110 will be further described with reference to FIGS. 2 through 5. Although a few embodiments of the present invention have been shown and described, various changes may be made to graphical configurations, and other multiple factors unrelated to the spirit of the invention.

Figure 2:
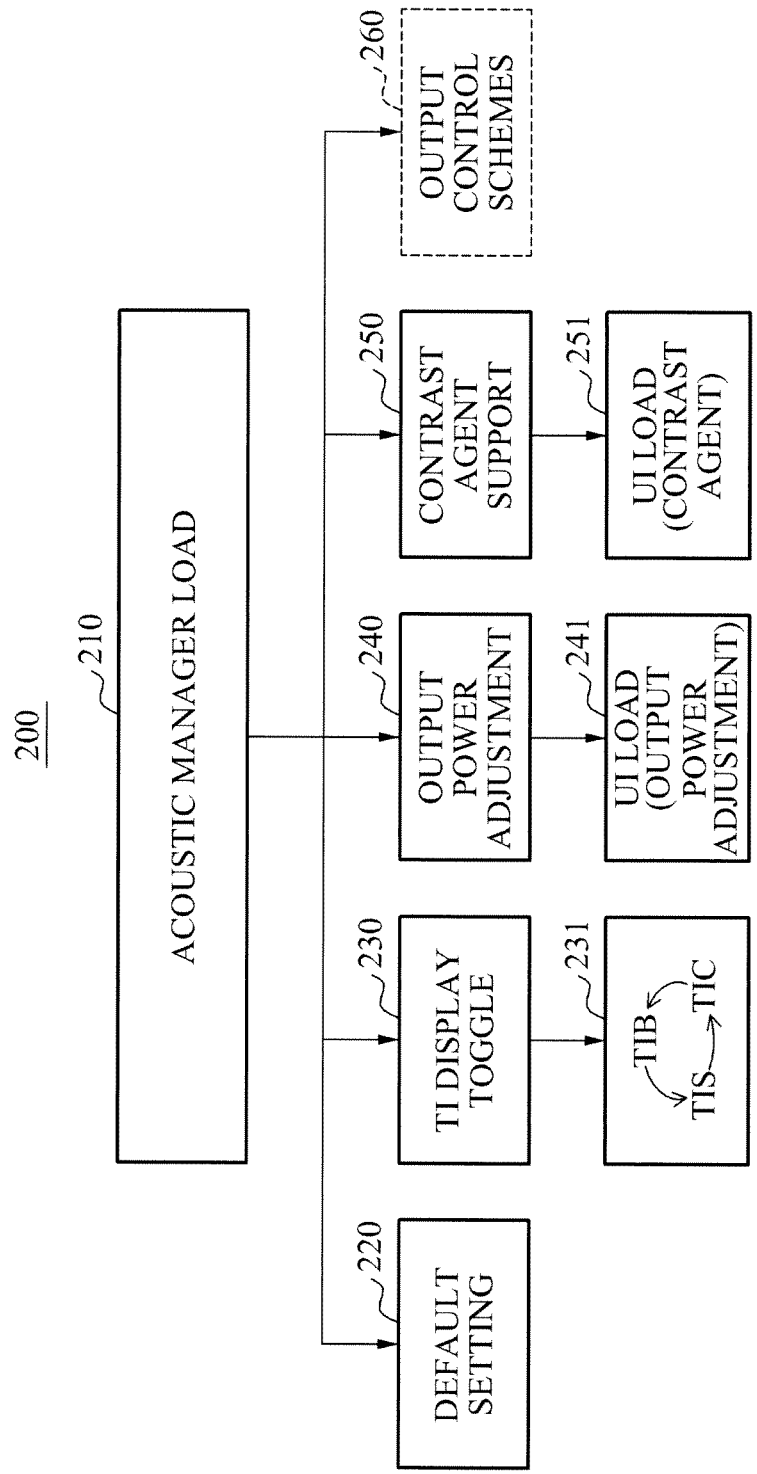
FIG. 2 is a diagram illustrating an example of a user interface (UI) provided for an output control in an ultrasonic diagnosis apparatus according to an embodiment of the present invention.

FIG. 2 is a diagram 200 illustrating an example of a user interface (UI) provided for an output control in an ultrasonic diagnosis apparatus according to an embodiment of the present invention.

There may be provided an acoustic output manager load 210, and may be also provided menus corresponding to default settings 220, a TI display toggle 230, an output power adjustment 240, a contrast agent support 250, and output control schemes 260, as sub-menus.

The default settings 220 may set an output level to a default as described above.

The TI display toggle 230 may perform toggles, such as TIb, TIs, TIc, and the like, and there may be provided a UI load 241 for output power adjustment, in the output power adjustment 240, which will be further described with reference to FIG. 3.

Also, in the contrast agent support 250, there may be provided a setting UI load 251 according to a contrast agent, which will be further described with reference to FIG. 4.

Figure 3:
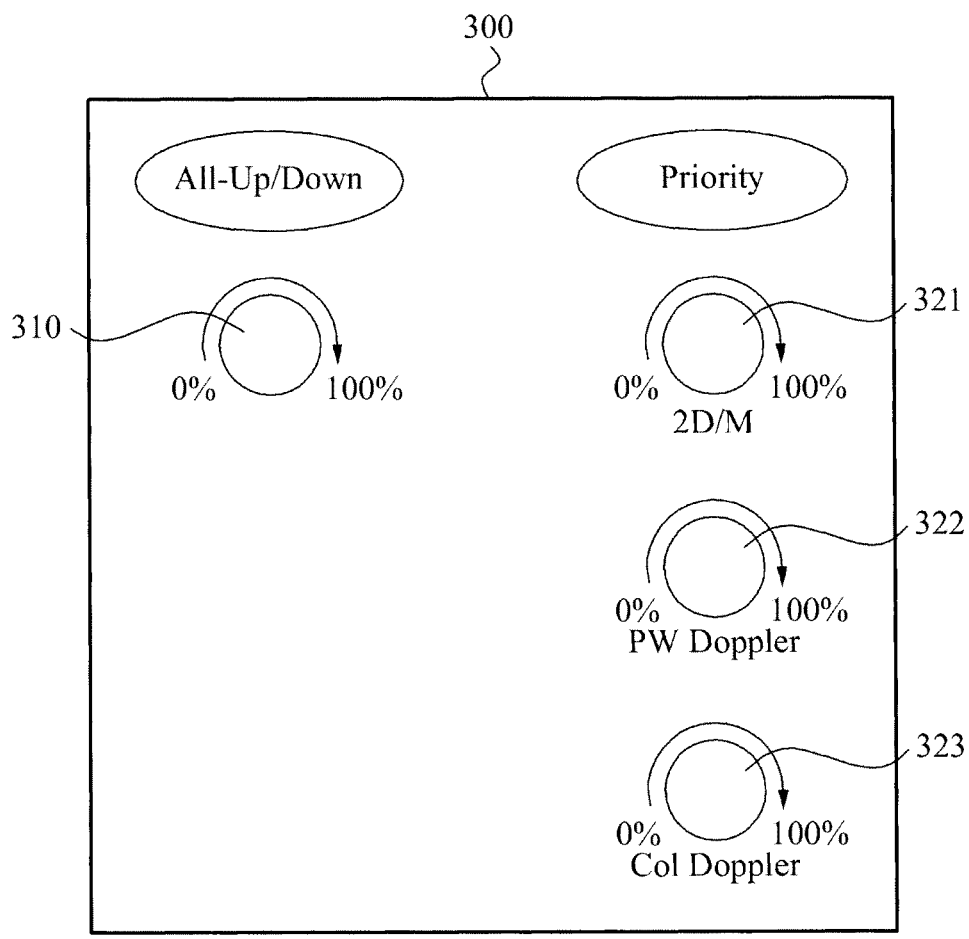
FIG. 3 is a diagram illustrating another example of a UI provided for an output control in an ultrasonic diagnosis apparatus according to an embodiment of the present invention.

FIG. 3 is a diagram 300 illustrating another example of a user interface (UI) provided for an output control in an ultrasonic diagnosis apparatus according to an embodiment of the present invention.

In FIG. 2, when the UI load 241 for the output power adjustment is selected, a Graph User Interface (GUI) may be provided as illustrated in the diagram 300.

The user may adjust an overall output to be within a range of below 100%, using an interface 310. A processing procedure in case of receiving a command to increase the overall output, or to lower the overall output using the interface 310 may be similar as described with reference to FIG. 1.

During a combinational mode operation, all of interfaces 321 through 323, or a part of the interfaces 321 through 323 may be selectively provided. Then, the user may control an individual output using the interfaces 321 through 323.

Figure 4:
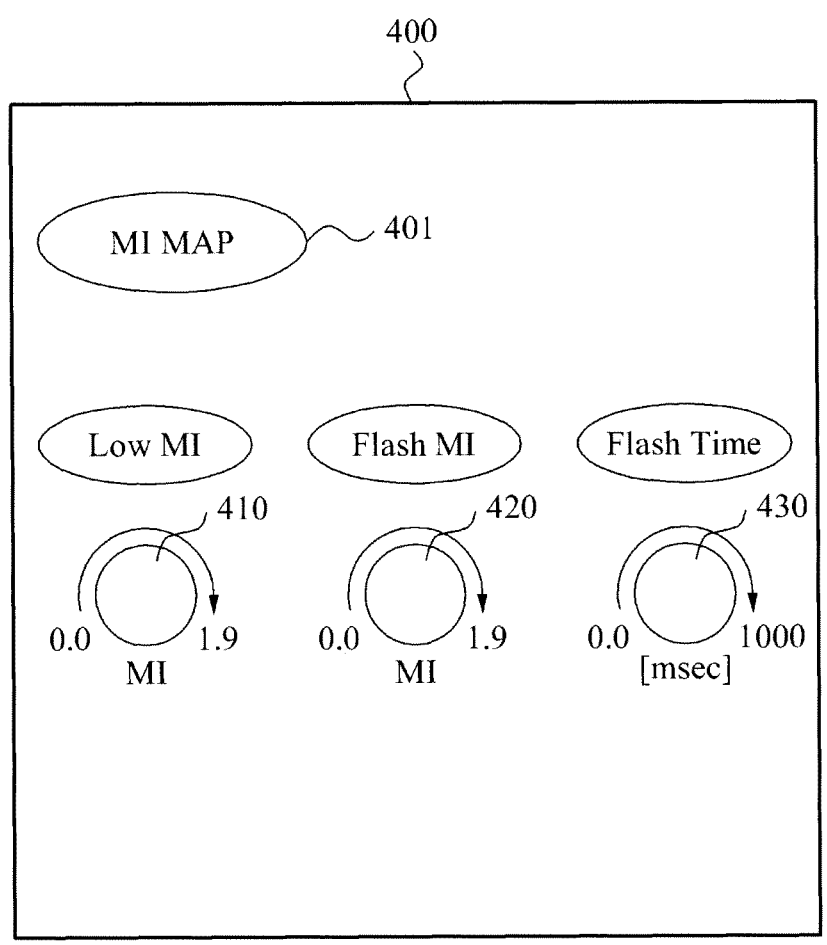
FIG. 4 is a diagram illustrating another example of a UI provided for an output control in an ultrasonic diagnosis apparatus according to an embodiment of the present invention.

FIG. 4 is a diagram 400 illustrating another example of a user interface (UI) provided for an output control in an ultrasonic diagnosis apparatus according to an embodiment of the present invention.

There may be provided an MI map that may graphically indicate an MI with respect to a current operation, by an interface 401.

The user may separately adjust a Low MI, a Flash MI, and the like using interfaces 410 through 430, in response to a contrast agent, and may also control an output frame or a duty cycle as aforementioned with reference to FIG. 1.

Figure 5:
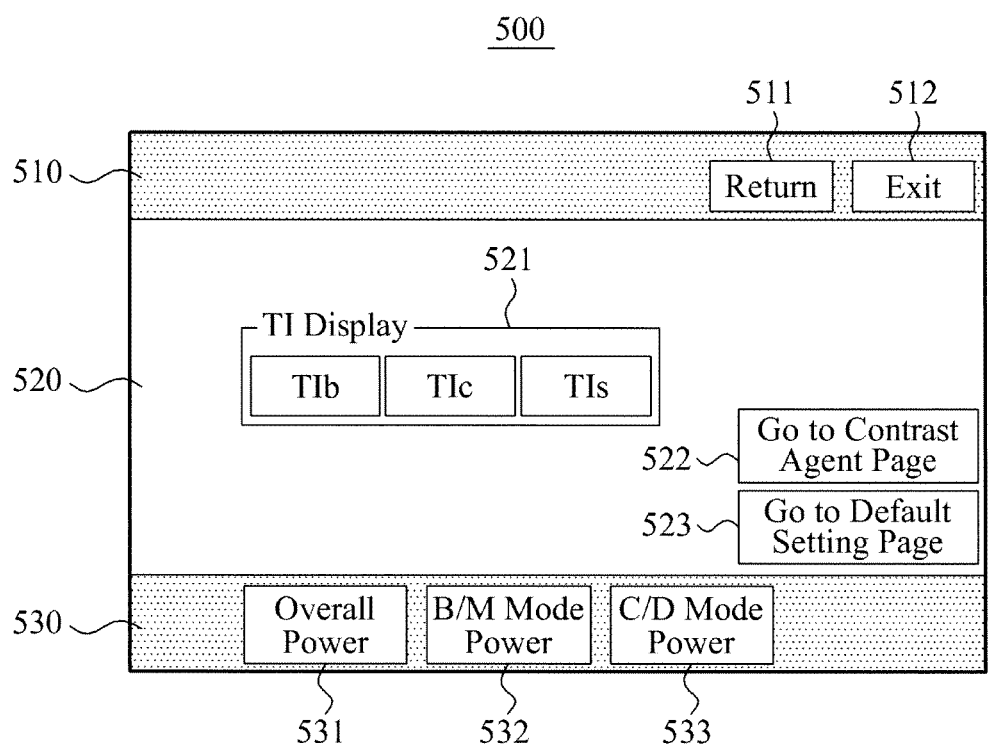
FIG. 5 is a diagram illustrating another example of a UI provided for an output control in an ultrasonic diagnosis apparatus according to an embodiment of the present invention.

FIG. 5 is a diagram 500 illustrating another example of a user interface (UI) provided for an output control in an ultrasonic diagnosis apparatus according to an embodiment of the present invention.

There may be provided a return interface 511, and an exit interface 512 for toggling interfaces in an area 510, and there may be provided a TI display interface 521, a contrast agent page interface 522, and a default setting page interface 523 in an area 520.

The portion with respect to the TI display, provided in a toggle form in FIG. 3, may be currently provided as a selective button interface 521.

In an area 530, there may be provided interfaces 531 through 533 for enabling the overall output adjustment or the individual output adjustment that have been described with reference to FIG. 1.

Figure 6:
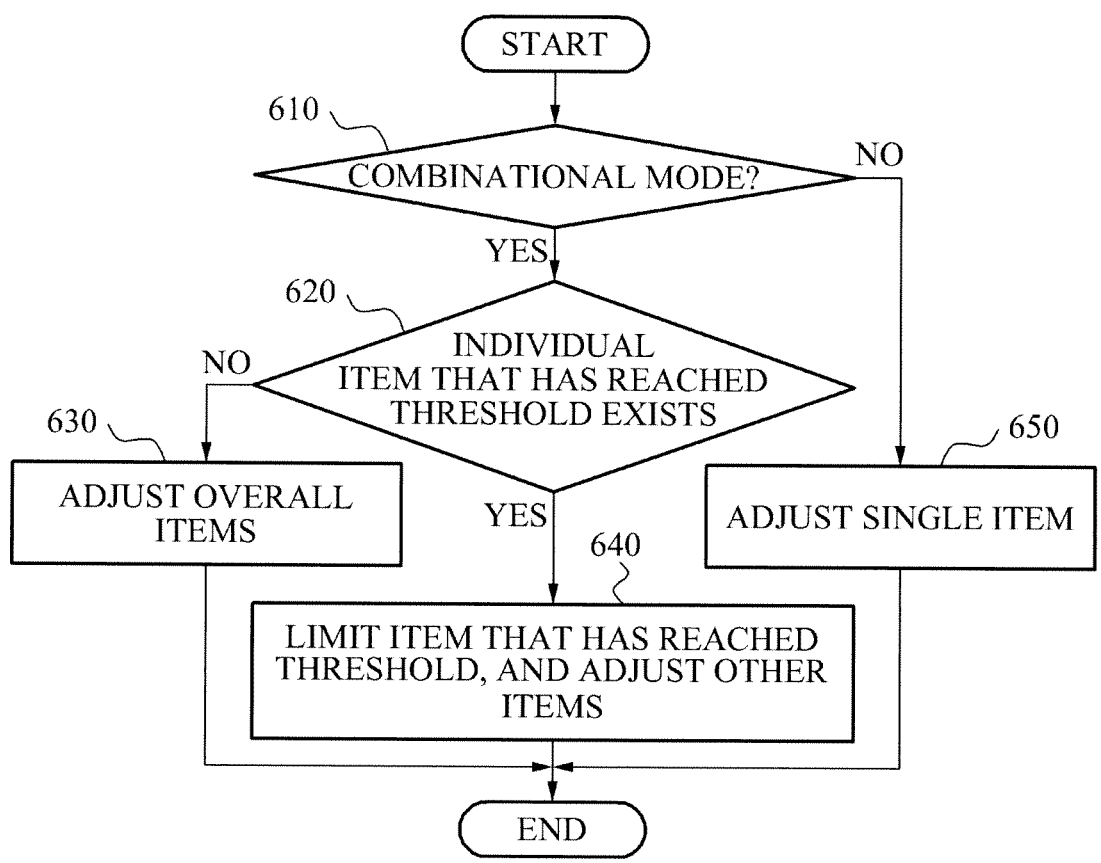
FIG. 6 is a flowchart illustrating a method of controlling an output of an ultrasonic diagnosis apparatus according to an embodiment of the present invention.

FIG. 6 is a flowchart illustrating a method of controlling an output of an ultrasonic diagnosis apparatus according to an embodiment of the present invention.

In operation 610, an overall output adjustment command may be received using the UI 110. Then, the judging unit 120 may first judge whether a current mode corresponds to a combinational mode.

In a case that the current mode corresponds to a single mode instead of the combinational mode, the UI 100 may provide only an interface with respect to an overall output control, without providing an interface with respect to an individual output control.

In the case of the single mode, the output control unit 130 may perform an adjustment of a single power in operation 650.

When the current mode is judged to correspond to the combinational mode in operation 610, the judging unit 120 may judge whether individual powers, for example, a B/M power, and the like may reach a permissible threshold with respect to safety standards, by the received overall output control command, in operation 620.

When there is an item of the individual power that may have reached the threshold, the output control unit 130 may limit the item, which may have reached the threshold, to be a value below the threshold, and may also adjust an output of the transducer 140 to satisfy the overall output control command with respect to other items only, in operation 640.

When there is no item of the individual power that may have reached the threshold in operation 620, the output control unit 130 may adjust outputs of overall items to satisfy the received overall output control command, in operation 630.

The detailed examples of the method of controlling the output may be similar to the above-described method, with reference to FIG. 1.

The above-described exemplary embodiments of the present invention may be recorded in computer-readable media including program instructions to implement various operations embodied by a computer. The media may also include, alone or in combination with the program instructions, data files, data structures, and the like. Examples of computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described exemplary embodiments of the present invention, or vice versa.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. An ultrasonic diagnosis apparatus that operates in a combinational mode including a first mode and other modes, the apparatus simultaneously providing a plurality of outputs of pulses having voltage levels corresponding to the first mode and the other modes using transducers in the combinational mode, the apparatus comprising:
   an output control unit configured to control the voltage levels of the plurality of outputs of individual pulses corresponding to the first mode and the other modes;
   a user interface (UI) configured to receive an output value control command to increase overall voltage levels of the plurality of outputs of the pulses corresponding to the first mode and the other modes from a user;
   a judging unit configured to judge whether the output value control command enables each of the voltage levels of the plurality of outputs corresponding to the first mode and the other modes to exceed a threshold determined by safety standards with respect to the first mode and the other modes, wherein:
   when the judging unit judges that the output value control command does not enable the voltage levels of the plurality of outputs corresponding to the first mode and the other modes to exceed thresholds, the output control unit is configured to increase the voltage levels of the plurality of outputs corresponding to the first mode and the other modes based on the output value control command, when the judging unit judges that the output value control command enables a voltage level of an output corresponding to the first mode to exceed a threshold and does not enable voltage levels of outputs corresponding to the other modes to exceed thresholds, the output control unit is configured to maintain the voltage level of the output corresponding to the first mode to be below the threshold and to increase the voltage levels of the outputs corresponding to the other modes based on the output value control command, and when the judging unit judges that the output value control command enables the voltage levels of the plurality of outputs corresponding to the first mode and the other modes to exceed thresholds, the output control unit is configured to maintain the voltage levels of the plurality of outputs corresponding to the first mode and the other modes to be below the thresholds.

2. The apparatus of claim 1, wherein the combinational mode is selected from the group consisting of a B+pD mode, a B+CD mode, and a B+pD+CD mode.

3. The apparatus of claim 1, wherein the output value control command increases voltages of the overall outputs of the transducer corresponding to the combinational mode, or lowers the voltages of the overall outputs of the transducer corresponding to the combinational mode, by a percentage unit.

4. The apparatus of claim 1, wherein the UI comprises:
a first output control interface corresponding to each of a plurality of modes included in the combinational mode: and
a second output control interface to adjust overall outputs of the plurality of the modes.

5. The apparatus of claim I, wherein the first mode corresponds to a B mode, and the safety standards with respect to the first mode correspond to a mechanical index (MI).

6. A method of controlling an output of an ultrasonic diagnosis apparatus that operates in a combinational mode including a first mode and other modes, the apparatus simultaneously providing a plurality of outputs of pulses having voltage levels corresponding to the first mode and the other modes using transducers in the combinational mode, the method comprising:
receiving, by a user interface (UI) of the ultrasonic diagnosis apparatus, an output value control command to increase overall voltage levels of the plurality of outputs of the pulses corresponding to the first mode and the other modes from a user;
judging, by a judging unit of the ultrasonic diagnosis apparatus, whether the output value control command enables each of the voltage levels of the plurality of outputs corresponding to the first mode and the other modes to exceed a threshold determined by safety standards with respect to the first mode and the other modes; and
controlling, by an output control unit of the ultrasonic diagnosis apparatus, the voltage levels of the plurality of outputs of individual pulses corresponding to the first mode and the other modes, wherein the controlling the voltage levels of the plurality of outputs comprises:
when it is judged that the output value control command does not enable the voltage levels of the plurality of outputs corresponding to the first mode and the other modes to exceed thresholds, increasing the voltage levels of the plurality of outputs corresponding to the first mode and the other modes based on the output value control command,
when it is judged that the output value control command enables a voltage level of an output corresponding to the first mode to exceed a threshold and does not enable voltage levels of outputs corresponding to the other modes to exceed thresholds, maintaining the voltage level of the output corresponding to the first mode to be below the threshold and increasing the voltage levels of the outputs corresponding to the other modes based on the output value control command, and
when it is judged that the output value control command enables the voltage levels of the plurality of outputs corresponding to the first mode and the other modes to exceed thresholds, maintaining the voltage levels of the plurality of outputs corresponding to the first mode and the other modes to be below the thresholds.

7. The method of claim 6, wherein the combinational mode is selected from the group consisting of a B+pD mode, a B+CD mode, and a B+pD+CD mode.

8. The method of claim 6, wherein the output value control command increases voltages of the overall outputs of the transducer corresponding to the combinational mode, or lowers the voltages of the overall outputs of the transducer corresponding to the combinational mode, by a percentage unit.

9. The method of claim 6, further comprising:
providing, by the UI, an output control interface corresponding to each of a plurality of modes included in the combinational mode, and the output control interface to adjust overall outputs of the plurality of the modes, in advance of receiving the output value control command.

10. The method of claim 6, wherein the first mode corresponds to a B mode, and the safety standards with respect to the first mode correspond to a mechanical index (MI).

* * * * *